US008895239B2

(12) United States Patent
Franciskovich et al.

(10) Patent No.: US 8,895,239 B2
(45) Date of Patent: Nov. 25, 2014

(54) GENETICALLY ENGINEERED BIOLOGICAL INDICATOR

(75) Inventors: Phillip P. Franciskovich, Concord, OH (US); William A. Yirava, Willoughby, OH (US); Tricia A. Cregger, Fairlawn, OH (US)

(73) Assignee: American Sterilizer Company, Mentor, OH (US)

( * ) Notice: Subject to any disclaimer, the term of this patent is extended or adjusted under 35 U.S.C. 154(b) by 727 days.

(21) Appl. No.: 11/533,522

(22) Filed: Sep. 20, 2006

(65) Prior Publication Data

US 2008/0070231 A1 Mar. 20, 2008

(51) Int. Cl.
*C12N 1/20* (2006.01)
*C12N 15/75* (2006.01)
*C12N 9/38* (2006.01)

(52) U.S. Cl.
CPC .......... *C12N 15/75* (2013.01); *C12Y 302/01023* (2013.01); *C12N 9/2471* (2013.01)
USPC ......................................... 435/6.1; 435/252.1

(58) Field of Classification Search
CPC .................................. C12N 1/00; C12N 1/21
USPC ................................ 435/252.1, 252.6, 253.6
See application file for complete search history.

(56) References Cited

U.S. PATENT DOCUMENTS

| | | | | |
|---|---|---|---|---|
| 2,854,384 A | 9/1958 | Beakley et al. | ................. | 195/54 |
| 3,239,429 A | 3/1966 | Menolasino et al. | ........... | 195/54 |
| 3,346,464 A | 10/1967 | Ernst | ................ | 195/54 |
| 3,440,144 A | 4/1969 | Andersen | ................... | 195/103.5 |
| 3,551,295 A | 12/1970 | Dyer | .......................... | 195/103.5 |
| 3,585,112 A | 6/1971 | Ernst | ........................ | 195/103.5 |
| 3,661,717 A | 5/1972 | Nelson | ....................... | 195/103.5 |
| 3,752,743 A | 8/1973 | Henshilwood | ................ | 195/127 |
| 3,796,635 A | 3/1974 | Delente | .......................... | 195/65 |
| 3,846,242 A | 11/1974 | Ernst | ........................ | 195/103.5 |
| 4,011,139 A | 3/1977 | Horwath et al. | ................ | 195/65 |
| 4,162,942 A | 7/1979 | Gunther | .......................... | 435/17 |
| 4,284,719 A | 8/1981 | Agerhem et al. | ............... | 435/18 |
| 4,291,122 A | 9/1981 | Orelski | ........................ | 435/31 |
| 4,304,869 A | 12/1981 | Dyke | .......................... | 435/296 |
| 4,348,209 A | 9/1982 | Murtaugh et al. | ............... | 23/232 |
| 4,416,984 A | 11/1983 | Wheeler, Jr. | .................... | 435/31 |
| 4,448,548 A | 5/1984 | Foley | ........................ | 374/160 |
| 4,461,837 A | 7/1984 | Karle et al. | ................... | 435/296 |
| 4,528,268 A | 7/1985 | Andersen et al. | ............... | 435/31 |
| 4,579,823 A | 4/1986 | Ryder | .......................... | 435/296 |
| 4,580,682 A | 4/1986 | Gorski et al. | ................ | 206/569 |
| 4,591,554 A | 5/1986 | Koumura et al. | ............... | 435/18 |
| 4,596,773 A | 6/1986 | Wheeler, Jr. | .................... | 435/31 |
| 4,603,108 A | 7/1986 | Bascomb | ........................ | 435/34 |
| 4,883,641 A | 11/1989 | Wicks et al. | ................... | 422/50 |
| 5,073,488 A | 12/1991 | Matner et al. | .................... | 435/31 |
| 5,079,144 A | 1/1992 | Carr et al. | ........................ | 435/32 |
| 5,223,401 A | 6/1993 | Foltz et al. | .................... | 435/18 |
| 5,252,484 A | 10/1993 | Matner et al. | ................. | 435/288 |
| 5,366,872 A | 11/1994 | Hird et al. | ........................ | 435/31 |
| 5,418,167 A | 5/1995 | Matner et al. | ................. | 435/288 |
| 5,486,459 A | 1/1996 | Burnham et al. | ............... | 435/31 |
| 5,739,004 A | 4/1998 | Woodson | ........................ | 435/31 |
| 5,770,393 A | 6/1998 | Dalmasso et al. | ............... | 435/31 |
| 5,830,683 A | 11/1998 | Hendricks et al. | .............. | 435/31 |
| 5,870,885 A | 2/1999 | Biddle et al. | .................... | 53/436 |
| 5,989,852 A | 11/1999 | Hendricks et al. | .............. | 435/31 |
| 6,025,189 A | 2/2000 | Bolea et al. | ................. | 435/287.4 |
| 6,063,591 A | 5/2000 | Bolea | .............................. | 435/31 |
| 6,329,160 B1 | 12/2001 | Schneider et al. | ........... | 435/7.31 |
| 6,355,448 B1 | 3/2002 | Foltz et al. | ........................ | 435/31 |
| 6,566,090 B2 | 5/2003 | Witcher et al. | .................... | 435/31 |
| 6,576,422 B1 | 6/2003 | Weinstein et al. | ................. | 435/6 |
| 6,623,955 B2 | 9/2003 | Matner et al. | .............. | 435/287.4 |
| 6,942,989 B2 | 9/2005 | Felkner et al. | ................... | 435/31 |
| 2003/0064507 A1 | 4/2003 | Gallagher et al. | .......... | 435/287.2 |
| 2007/0238145 A1 | 10/2007 | Cote et al. | ........................ | 435/29 |
| 2007/0269838 A1* | 11/2007 | Lee et al. | ..................... | 435/7.31 |
| 2008/0199903 A1* | 8/2008 | Cregger et al. | ................. | 435/31 |

FOREIGN PATENT DOCUMENTS

| | | |
|---|---|---|
| EP | 0000063 A1 | 12/1978 |
| EP | 1201255 | 5/2002 |
| GB | 1547747 A | 6/1979 |
| GB | 2128204 A | 4/1984 |
| GB | 2186974 A | 8/1987 |
| WO | 8605206 A1 | 9/1986 |
| WO | 9920790 | 4/1999 |

OTHER PUBLICATIONS

Chao et al. Applicability of new expression vectors for both engineering uses and biological studies. Biotechnol. Prog. 19: 1076-1080, 2003.*
Rygus et al. Molecular cloning, structure, promoters and regulatory elements for transcription of the *Bacillus licheniformis* encoded regulon for xylose utilization. Arch Microbiol. 155: 535-542, 1991.*
Hinnebusch et al. Linear plasmids and chromosomes in bacteria. Mol. Micro. 10(5): 917-922, 1993.*
Papinutto et al. Structure of Two Iron-Binding Proteins from *Bacillus anthracis*. J. Biol. Chem. 277(17): 15093-15098, 2002.*
Bhavsar et al. Development and characterization of a xylose-dependent system for expression of cloned genes in *Bacillus subtilis*: conditional complementation of a teichoic acid mutant. Appl Environ Microbiol. Jan. 2001;67(1):403-10.*

(Continued)

*Primary Examiner* — Michele K Joike
(74) *Attorney, Agent, or Firm* — Renner, Otto, Boisselle & Sklar, LLP

(57) ABSTRACT

The disclosed technology relates to a genetically engineered biological indicator, comprising: at least one test organism and at least one reporter gene suitable for producing an indicator enzyme, the reporter gene being taken up by the test organism; and at least one repressor gene that inhibits expression of the reporter gene until the reporter gene is exposed to at least one inducer. A process and an apparatus for using the biological indicator are disclosed.

35 Claims, 4 Drawing Sheets

(56) References Cited

OTHER PUBLICATIONS

Yuan et al. Regulation of groE expression in *Bacillus subtilis*: the involvement of the sigma A-like promoter and the roles of the inverted repeat sequence (CIRCE). J Bacteriol. Oct. 1995;177(19):5427-33.*

U.S. Appl. No. 11/533,487, filed Sep. 20, 2006.

International Search Report and Written Opinion; Application No. PCT/US07/78828, mailed Jun. 26, 2008.

Geoffrey Zubay; Biochemistry, Third Edition; Wm. C. Brown Publishers, 1993; pp. 867 and 868.

Haruhisa Hirata et al.; Journal of Bacteriology, "Structure of a β-Galactosidase Gene of *Bacillus stearothermophilus*"; Jun. 1986; pp. 722-727.

Haruhisa Hirata et al.; Applied and Environmental Microbiology, "High Production of Thermostable β-Galactosidase of *Bacillus stearothermophilus* in *Baccilus subtilis*"; Jun. 1985; pp. 1547-1549.

Tohru Shimizu et al.; Proceedings of the National Academy or Sciences of the United States of America, vol. 99, No. 2, "Complete Genome Sequence of *Clostridium perfringens*, an Anaerobic Flesh-eater"; Jan. 2002; pp. 996-1001.

J. Hahn et al.; Molecular Microbiology, "Regulatory Inputs for the Synthesis of ComK, the Competence Transcription Factor of *Bacillus subtilis*"; 1996; pp. 763-775.

N.E. Welker et al.; "Induction of α-Amylase of *Bacillus stearothermophilus* by Maltodextrins"; J. Bacteriol, vol. 86, Apr. 1963; pp. 687-691.

http://textbookofbacteriology.net/regulation.html; Kenneth Todar University of Wisconsin-Madison Department of Bacteriology; "Regulation and Control of Metabolic Activity"; 2004; pp. 1-11.

http://textbookofbacteriology.net/nutgro.html; Kenneth Todar University of Wisconsin-Madison Department of Bacteriology; "Nutrition and Growth of Bacteria"; 2004; pp. 1-17.

Supplemental European Search Report, Application No. 07872302.0, dated Mar. 3, 2010.

Hansen et al.; "Detection of Oxytetracycline Production by *Streptomyces rimosus* in Soil Microcosms by Combining Whole-Cell Biosensors and Flow Cytometry"; Applied and Environmental Microbiology; vol. 67, No. 1, Jan. 2001; pp. 239-244.

Miller et al.; "Biological Sensor of Sucrose Availability: Relative Sensitivities of Various Reporter Genes"; Applied and Environmental Microbiology; vol. 67, No. 3; Mar. 2001; pp. 1308-1317.

* cited by examiner

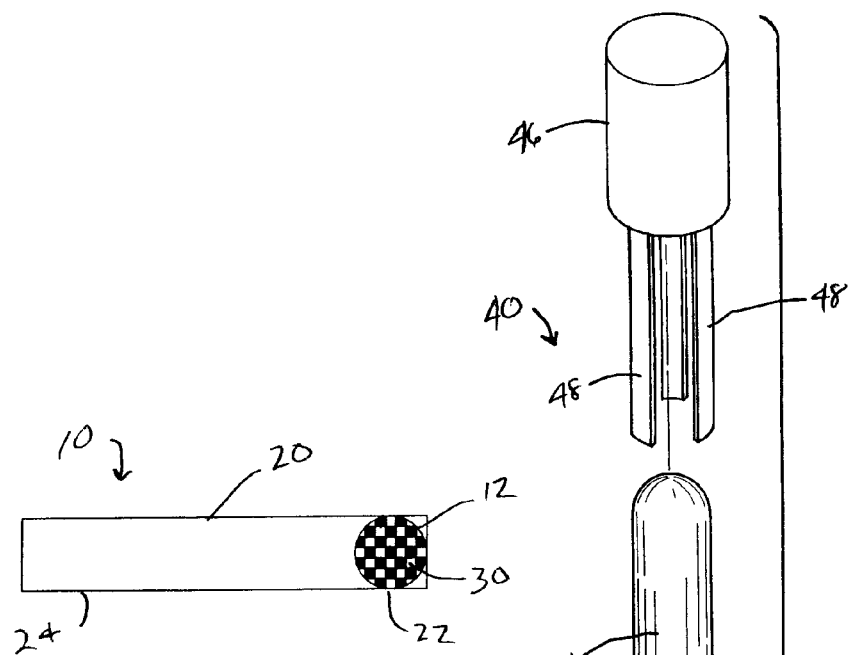
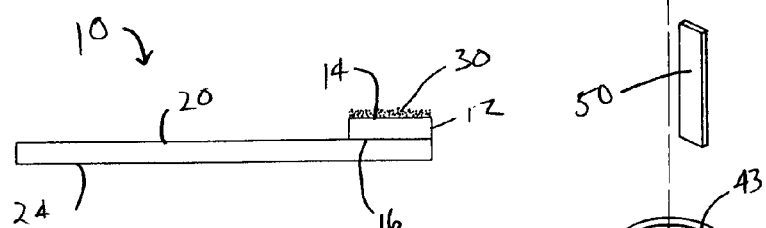
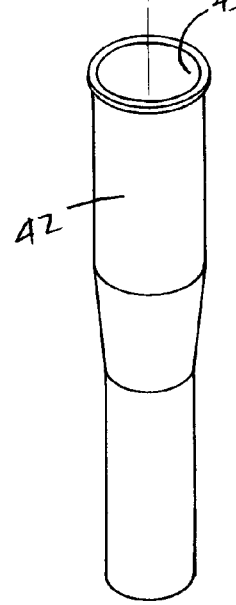
FIG. 5
FIG. 6
FIG. 7

GENETICALLY ENGINEERED BIOLOGICAL INDICATOR

TECHNICAL FIELD

The disclosed technology relates to genetically engineered biological indicators. These biological indicators may be useful for determining the effectiveness of one or more sterilization processes.

BACKGROUND

Primarily in the health care industry, but also in many other commercial and industrial applications, it is often necessary to monitor the effectiveness of the processes used to sterilize equipment such as medical and non-medical devices, instruments and other articles and materials. It is often standard practice in these sterilization processes to include a sterilization indicator in the batch of articles to be sterilized. This allows a direct approach to assay the lethality of the sterilization process.

Classical methods of sterility assurance typically involve exposing a sterilization indicator containing one or more test organisms to the sterilization process and then measuring the outgrowth of any surviving test organisms. Sterility may be assured if there is no outgrowth of the test organisms following exposure to the sterilization process. Bacterial spores (e.g., *Geobacillus stearothermophilus, Bacillus subtilis, Bacillus atrophaeus*, and the like) are typically used as the test organisms. Upon completion of the sterilization process, the sterilization indicator is exposed to a liquid growth support medium under conditions that would promote the growth of any surviving test organism cells. The growth support medium often contains a chemical dye which changes color in response to actively growing (metabolizing) cells. Because of the requirement for growth and metabolism, the processes employing these test organisms typically require about 24 to 72 hours of incubation before the effectiveness of the sterilization process can be determined. A problem with this process relates to the fact that many users of sterilized articles, such as health care facilities and the like, have limited resources and may reuse the "sterilized" articles within 24 to 72 hours and sometimes immediately. In such settings, the 24 to 72 hour holding period for sterility verification may be impractical, costly and inefficient.

A detection process for reading out test results more rapidly for certain 121° C. and 132° C. gravity and prevacuum steam sterilization cycles and ethylene oxide sterilization cycles has been proposed. The time necessary to observe evidence of surviving indicator cells is reported to be as little as one hour. This process is believed to involve detecting the catalytic activity of the enzyme alpha glucosidase. This enzyme may be produced by a microorganism as a normal component of its metabolism and may be present in the spore coat of the microorganism both before and during sterilization. The presence of this enzyme may be detected by reading fluorescence produced by the breakdown of a non-fluorescent enzyme substrate. This requires the use of a fluorometric auto-reader. Breakdown of the enzyme substrate may be an early detection alternative to waiting for a visual pH color change to indicate a failed sterilization process. Neither growth nor metabolism is required for the fluorometric signal. This results in a reduction in the time required to observe a failure in the sterilization process. However, the enzyme alpha glucosidase, which is thermophilic in origin, may be more resistant to heat than the microorganism from which it is derived. This may lead to nuisance failures, a circumstance in which the test microorganism has been, in fact, killed but the indicator enzyme indicates that the test microorganism remains viable. In addition, since the enzyme alpha glucosidase may be present in the spore coat of the test microorganism and its presence does not necessitate metabolism, the detection of this enzyme may not be a direct indication of life.

There are situations where the use of the enzyme alpha glucosidase may fail to discriminate an unsuccessfully sterilized load. Successful steam sterilization is dependent upon achieving an effective temperature and pressure for a minimum length of time. Bacterial spores are typically selected as the test organism for this process because they are highly resistant to this combination of parameters. It takes a particularly lethal combination of temperature, pressure and time to kill bacterial spores. Although the target/reporter molecule (alpha glucosidase) is a catalytic enzyme derived from a thermophilic organism, and thus somewhat resistant to heat, it is the heat of the process which ultimately destroys the function of the enzyme. That is, pressure and time play a reduced role in the denaturation of alpha glucosidase. Therefore, under sub-lethal pressure or time conditions the indicator enzyme might be destroyed even though the bacterial spores might not be destroyed. This may result in a failure to detect a non-sterilized load.

The inability of existing technology to account for all the parameters relating to cell death means that "grow out" may be required to provide the final confirmatory result. However, a major drawback with processes requiring what is traditionally known as grow out relates to the time delay in obtaining results for the sterilization test. Sterilization indicators requiring grow out normally employ the use of bacterial spores which must be cultured for at least about 24 to 72 hours to assure adequate detection of any surviving spores. During this time, the articles that went through the sterilization process and are under evaluation should not be used until the results of the spore viability test have been determined. However, as indicated above, this is impractical for many users of articles requiring sterilization.

Thus, a problem that has been presented by the art is to provide a biological indicator that accurately and directly detects the effectiveness of a sterilization process within a relatively short period of time. The disclosed technology provides a solution to this problem.

SUMMARY

The disclosed technology relates to a genetically engineered biological indicator, comprising: at least one test organism and at least one reporter gene suitable for producing an indicator enzyme, the reporter gene being taken up by the test organism; and at least one repressor gene that inhibits expression of the reporter gene until the reporter gene is exposed to at least one inducer.

The disclosed technology relates to a sterilization process, comprising: exposing an article to be sterilized and the above-indicated biological indicator to a sterilization medium.

The disclosed technology relates to a process for determining the effectiveness of a sterilization process, comprising: exposing at least one article to be sterilized and a sterilization indicator comprising the above-indicated biological indicator to a sterilization medium; and contacting the sterilization indicator with at least one inducer and at least one enzyme substrate to determine whether the sterilization is effective.

The disclosed technology relates to a sterilization indicator, comprising: a carrier, the carrier having a first surface and a second surface; a support, the support having a first section and a second section, the carrier overlying the first section of the support, the second surface of the carrier being adhered to the first section of the support; and the above-indicated genetically engineered biological indicator being supported by the carrier, the second section of the support being of sufficient dimension to permit handling the sterilization indicator without contacting the biological indicator.

The disclosed technology relates to a sterilization indicator, comprising: a first compartment containing the above-indicated genetically engineered biological indicator, the first compartment being adapted to permit the biological indicator to be brought into contact with a sterilization medium during sterilization; and a second compartment containing at least one inducer and at least one enzyme substrate, the second compartment being adapted to maintain the inducer and the enzyme substrate separate from the biological indicator during sterilization, and the second compartment being adapted to permit the inducer and the enzyme substrate to contact the biological indicator after the biological indicator has been exposed to the sterilization medium.

BRIEF DESCRIPTION OF THE DRAWINGS

In the annexed drawings, like parts and features have like references.

FIG. 5 is a plan view of a schematic illustration of a sterilization indicator that may be used for supporting the disclosed biological indicator.

FIG. 6 is a schematic illustration of a side elevation of the sterilization indicator depicted in FIG. 5.

FIG. 7 is an exploded schematic illustration of a sterilization indicator for determining the effectiveness of sterilization, the sterilization indicator containing two compartments, the foregoing biological indicator being positioned in one compartment and at least one inducer and at least one enzyme substrate being positioned in the other compartment.

DETAILED DESCRIPTION

Figure 1:
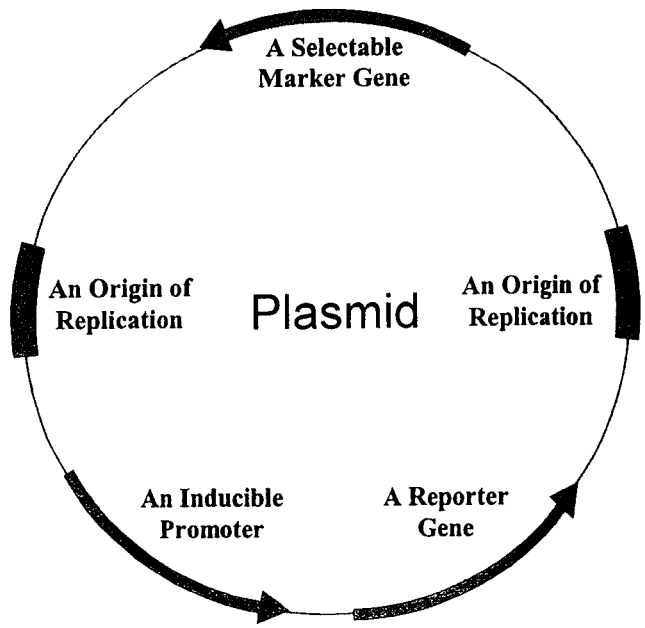
FIGS. 1-3 are diagrams of plasmid constructs that may be used to form the disclosed genetically engineered biological indicator.

The term "sterilization" refers to rendering a substance incapable of reproduction, metabolism and/or growth. While this is often taken to mean total absence of living organisms, the term may be used herein to refer to a substance free from living organisms to a degree previously agreed to be acceptable. Unless otherwise indicated, the term sterilization may be used herein to also refer to methods and procedures less rigorous than sterilization, for example, disinfection, sanitization, and the like. The genetically engineered biological indicator and the processes and apparatus described herein may be used in health care fields, scientific fields, and the like. These may be used in commercial and industrial applications where sterilization, disinfection, sanitization, decontamination, cleaning, and the like, may be desired. The commercial and industrial applications may include processes such as food processing, pasteurization, soil remediation, water remediation, and the like.

The sterilization process for which the disclosed sterilization indicator may be used may comprise any sterilization process. The sterilization process may include sterilization processes wherein the sterilization medium or sterilant may comprise steam, dry heat, radiation, plasma, as well as one or more gaseous sterilants, one or more liquid sterilants, and the like. The radiation may comprise electron beam or any electromagnetic spectra including ionizing radiation, pulsed white or ultraviolet light, microwave, and the like. The radiation may comprise gamma or beta radiation. The gaseous sterilants may comprise ethylene oxide, gaseous hydrogen peroxide, and the like. The liquid sterilants may comprise formalin (formaldehyde gas dissolved in water and optionally containing methanol to inhibit the formation of toxic substances), glutaraldehyde, peracetic acid, liquid hydrogen peroxide, and the like.

The genetically engineered biological indicator may be used to examine the lethality of sterilants against any microorganism with less resistance to the sterilization process than the test organism provided with the genetically engineered biological indicator. These microorganisms may include bacteria such as *Escherichia coli*, *Legionella* sp., *Campylobacter* sp., and other enteric bacteria, as well as *Staphylococcus* and *Streptococcus* species and other human pathogenic microorganisms such as *Cryptosporidium*.

The growth of an organism may comprise the combined result of a multitude of cellular processes. In typical sterilization indicator applications this may be observed in several ways. As cells grow and divide their individual numbers increase to a point at which the support medium of the cells may change from clear to opaque (turbid). To facilitate this observation of growth, a pH indicator dye may be used. Growth requires energy. This energy may be provided by the ability of the cell to metabolize nutrients contained in the support medium. The breakdown products of this process may cause the support medium to become acidic. This acidity may induce a pH indicator dye (e.g., phenol red) to change color. As a result, growth may be observed as the conversion of the support medium from a clear red to yellow color, for example, to a turbid yellow condition. Although these processes are slow, they represent compelling evidence of life and are generally accepted as the benchmark by the various sterility assurance regulatory bodies. By indirectly measuring viability as a function of the activity of a target/reporter enzyme (e.g., alpha glucosidase), it is possible to shorten the time required to get an indication of sterility. However, as indicated above, this process may still require grow out as the ultimate confirmation. Because growth and the accumulation of metabolic waste products are the end result of life processes, they may require significant time (24 to 72 hours) to become apparent With the present invention, a reporter gene (e.g., lacZ) suitable for producing an indicator enzyme (e.g. β-galactosidase) may be taken up by a test organism (e.g., a bacterial microorganism) using a suitable vehicle (e.g., plasmid or virus). Expression of the reporter gene may be actively blocked by a repressor gene (e.g., xylR). Expression of the reporter gene may remain blocked until the repressor gene is exposed to an inducer (e.g., xylose) which may be present in the recovery medium. Since the test organism is not exposed to the inducer until after the sterilization process has been completed, the indicator enzyme may not exist prior to or during sterilization. This means that no correlation between the susceptibility of the test organism and that of the indicator enzyme to the sterilization process may be required. What may be exposed to the sterilization process are the various and vital mechanisms the test organism uses to survive and grow and which are also used for the production of the indicator enzyme. These may include the DNA polymerases used for cellular growth (and replication of the plasmid), RNA polymerases for transcription of the metabolic requirements of the test organisms (and the plasmid or virus borne reporter gene, e.g., lacZ) and the ribosomal polysomes required for the translation of cellular proteins (as well as the expression of the indicator enzyme). Because the indicator enzyme may be fast acting as a signal generating mechanism, the presence of any remaining viable organisms may become apparent earlier than if they were tied to the accumulated end results of the vital growth mechanisms of the test organism.

The test organism may comprise any organism whose resistance to the intended sterilization process exceeds that of the other organisms that are to be destroyed by the sterilization process. The type of test organism used may be dependent upon a variety of factors exemplified by, but not limited to, the type of sterilization process being used. The test organism may be a microorganism. The strains that may be used may be those that are the most resistant to the process used for sterilization. The test organism may comprise one or more bacteria, pathogens, gram negative organisms, gram positive organisms, vegetative organisms, viruses, non self-replicating agents, sub-cellular components or products of cells, and/or prions. The bacterial microorganisms may be those which form endospores, i.e., bacterial spores. The test organism may comprise bacteria of the *Bacillus, Geobacillus* or *Clostridia* genera. These may include *Geobacillus stearothermophilus, Bacillus atrophaeus, Bacillus subtilis, Bacillus sphaericus, Bacillus anthracis, Bacillus pumilus, Bacillus coagulans, Clostridium sporogenes, Clostridium difficile, Clostridium botulinum, Bacillus subtilis globigii, Bacillus cereus, Bacillus circulans, Escherichia coli*, and the like. The bacteria may comprise fungi, mycobacteria, protozoa, vegetative bacteria, and the like. Examples of fungi that may be used may include *Aspergillus niger, Candida albicans, Trichophyton mentagrophytes, Wangiella dermatitis*, and the like. Examples of mycobacteria that may be used may include *Mycobacterium chelonae, Mycobacterium gordonae, Mycobacterium smegmantis, Mycobacterium terrae, Mycobacterium bovis, Mycobacterium tuberculosis*, and the like. Examples of protozoa that may be used may include *Giardia lamblia, Cryptosporidium parvum*, and the like. Examples of vegetative bacteria that may be used may include *Aeromonas hydrophila, Enterococcus faecalis, Streptococcus faecalis, Enterococcus faecium, Streptococcus pyrogenes, Escherichia coli, Klebsiella pneumoniae, Legionella pneumophila, Methylobacterium, Pseudomonas aeruginosa, Salmonella choleraesuis, Helicobacter pylori, Micrococcus radiodurans, Deinococcus radiodurans, Staphylococcus aureus, Staphylococcus epidermidis, Stenotrophomonas maltophilia*, and the like. Organisms such as *Geobacillus stearothermophilus, Bacillus atrophaeus, Bacillus subtilis, Bacillus coagulans, Clostridium sporogenes*, and the like, may be used for determining the efficacy of moist heat sterilization (autoclaving), with *Geobacillus stearothermophilus* being especially useful.

Vegetative organisms such as vegetative bacteria, vegetative cells and/or their constituent parts may be used as the test organism. Examples may include the coliform species and cells that do not form endospores e.g., *Aeromonas hydrophila, Enterococcus faecalis, Streptococcus faecalis, Enterococcus faecium, Streptococcus pyrogenes, Escherichia coli, Klebsiella* (pneumoniae), *Legionella pneumophila, Methylobacterium, Pseudomonas aeruginosa, Salmonella choleraesuis, Helicobacter pylori, Staphylococcus aureus, Staphylococcus epidermidis, Stenotrophomonas maltophilia*, and the like. These may be used in combination with one or more excipients. Excipients may be defined as a broad class of generally inert compounds that may be used to stabilize labile entities. A subclass of excipients that may be used includes the carbohydrates, for example, oligomeric and polymeric saccharides. An example of such a compound may be trehalose which is a disaccharide. High concentrations of trehalose in the tissues of certain organisms may allow the organisms to survive in a state of water deficiency. Trehalose may be used to revive functional cellular components after dehydration. Trehalose may provide stability to membranes and other macromolecular structures essential to the viability of a cell under extreme environmental conditions (e.g., freeze drying). Other stabilizing excipient compounds may include simple sugars (e.g. sucrose, glucose, maltose, and the like) and long chain polymers (e.g. dextrans, starch, agarose, cellulose, and the like). Other non-carbohydrate based excipients may include proteins, phosphonates, buffering agents, waxes, lipids, oils as well as other hydrocarbon based materials.

The test indicator may comprise one or more non self-replicating agents and/or sub-cellular components or products of cells. These may be used because of their clinical significance or because of their use as agents of bioterrorism. These indicator materials may comprise cellular strains which may now have resistance to normal means of antibiotic treatment or chemical disinfection due to natural or man-made modifications. Examples of the former type may include VREs (Vancomycin Resistant enterococci), MSRAs (Methicillin Resistant *Staphylococcus aureus*), *Mycobacterium cheloni*, and the like. These may be used because the VREs and MRSAs have developed resistance to therapeutic countermeasures (e.g., antibiotic resistance) and *M. cheloni* has developed resistance to some modes of disinfection (e.g., glutaraldehyde resistance).

The test indicator may comprise one or more emerging organisms. These may represent a special risk or challenge to therapeutic course of action or disinfection. Examples of these indicator materials may include prions. Prions are not living organisms, per se, but their function as disease causing agents may be related to their structure and this structure/function relationship may be employed to determine their relative infectivity. Other non-autonomous agents (e.g. viruses) as well as sub cellular elements and proteinaceous prions may be used.

The reporter gene that is taken up by the test organism is provided for the purpose of producing the indicator enzyme and may comprise lacZ, bgaB, xylE, cat, gfp, or a mixture of two or more thereof. The term "lacZ" refers to a gene coding for β-galactosidase. The term "bgaB" refers to the gene coding for thermostable β-galactosidase from *G. stearothermophilus*. The term "xylE" refers to gene coding for catechol-2, 3-dioxygenase from *Pseudomouas putida*. The term "cat" refers to the gene coding for chloramphenicol acetyltransferase, e.g., from pC194. The term "pC194" refers to a particular plasmid construct. The term "gfp" refers to the gene for coding thermostable green fluorescent protein variants.

The repressor gene may be taken up by the test organism. The repressor gene may comprise xylR, lacI, tetR, or a mixture of two or more thereof. The term "xylR" refers to the regulator of the xylose operon. The term "lacI" refers to the regulator of the lac operon. The term "tetR" refers to the regulator of the tet operon. The thermostable counterparts of these may be used. The repressor gene may be used to actively block expression of the reporter gene until the reporter gene is exposed to the inducer, which may be present in the recovery medium. The repressor gene may be taken up by the test organism with the same vehicle used to insert the reporter gene in the test organism.

The vehicle for inserting the reporter gene and the repressor gene in the test organism may comprise one or more plasmids and/or one or more viruses. These vehicles may be referred to as vectors. The plasmids may comprise circular double-stranded DNA that are separate from chromosomal DNA. The plasmids may be linear. The size of the plasmids may be in the range from about 2000 to about 20000 base pairs (bp), and in one embodiment in the range from about 5000 to about 10000 bp. One or more copies (for example, from 1 to about 3000 copies, and in one embodiment from 1 to about 60 copies, and in one embodiment from about 20 to about 3000 copies) of the same plasmid may be taken up by a single cell of the test organism. The plasmids may contain one or more DNA sequences that serve as an origin of replication (ori). The plasmids may contain one or more genetic markers. The plasmids may contain a polylinker or multiple cloning site (MCS) which may be a relatively short region containing one or more restriction sites allowing the insertion of DNA fragments. The plasmids may contain one or more genes that provide a selective marker to induce the test organism to retain the plasmid. The selective marker may comprise an antibiotic resistance gene and/or or a gene with nutritional capability. The plasmids may comprise conjugative plasmids which contain tragenes which may perform the process of conjugation, the sexual transfer of plasmids to another bacterium.

Figure 2:
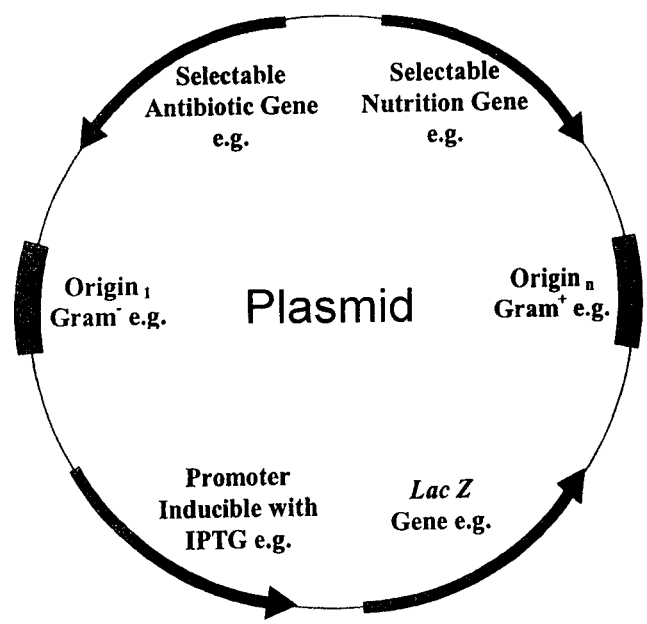

The plasmids may comprise at least one origin of replication, at least one selectable marker, at least one inducible promoter, and at least one reporter gene. Examples are illustrated in FIGS. 1 and 2. The selectable marker may comprise an antibiotic resistance gene and/or a gene with exogenous nutritional capability. These may include chloramphenicol, ampicillin or spectinomycin antibiotic resistance genes, and/or xylose or lactose nutritional genes. The inducible promoter may comprise PxylA. The term PxylA refers to a transcription promoter that requires xylose to remain active. The reporter gene may comprise lacZ, bgaB, xylE, cat, gfp, and the like. The plasmid may comprise two origins of replication. One of the origins of replication may comprise a gram negative origin of replication and the other origin of replication may comprise a gram positive origin of replication. The gram negative origin of replication may comprise *Escherichia coli*. The gram positive origin of replication may comprise *Bacillus subtilis, Geobacillus stearothermophilis* or *Bacillus atrophaeus*. The plasmids illustrated in FIGS. 1 and 2 may contain from about 2000 to about 20000 bp, and in one embodiment from about 5000 to about 10000 bp.

Figure 3:
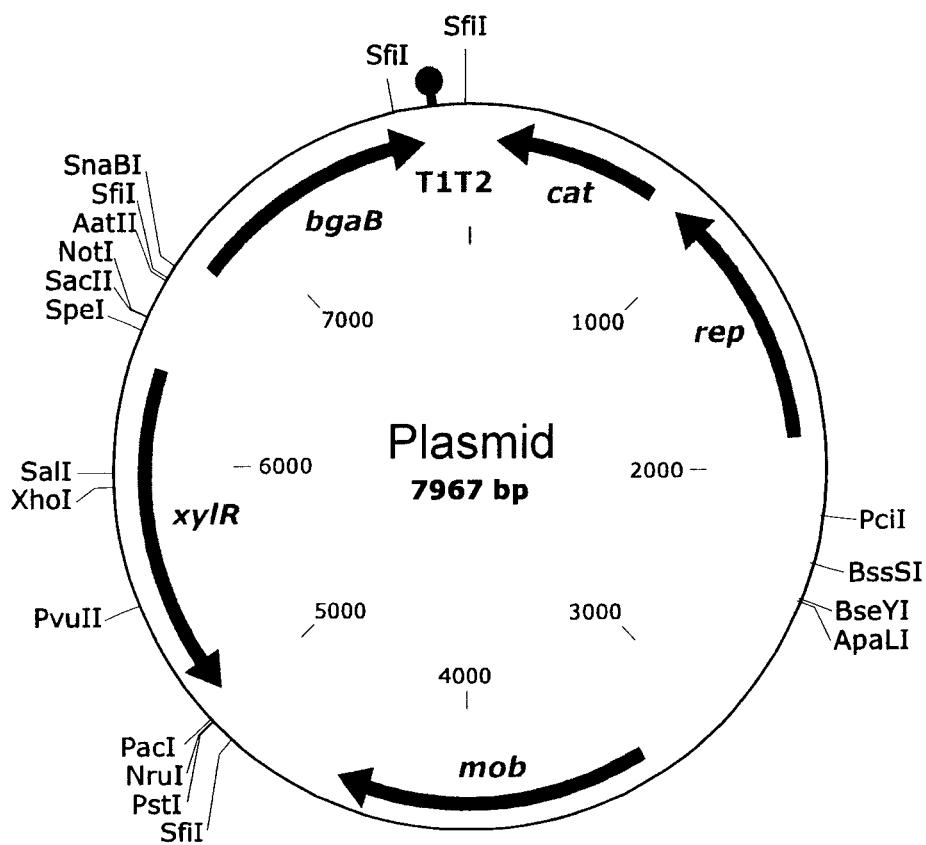

The plasmid may have the construction illustrated in FIG. 3. In FIG. 3, the following abbreviations are used:

"cat" refers to a segment of DNA containing the gene for chloramphemicol acelyltransferase from pC194.

"rep" refers to the genes for replication.

"mob" refers to mobility factor genes.

"xylR" refers to regulator of the xylose operon.

"bgaB" refers to the gene for thermostable β-galactosidase.

"T1T2" refers to terminators 1 and 2.

The terms "PciI," "BssSI," "BseYI," "ApaLI," "PstI," "NruI," "PacI," "PvuII," "XhoI," "SfiI," "SalI," "SpeI," "SacII," "NotI," "AatII," "SnaBI" refer to restriction endonuclease sites that occur within the DNA sequence of the plasmid depicted in FIG. 3. These sites represent cleavage points for various restriction endonucleases and are used in FIG. 3 as reference points. These sites may be used to help identify the plasmid. They may be used to cut the plasmid into its constituent parts. The plasmid illustrated in FIG. 3 has 7967 base pairs.

Naturally occurring plasmids exist over a broad range of host organisms in nature. They may comprise genes, regulatory elements and/or structural pieces of DNA. Plasmids usually provide some advantage to their host organism (e.g. antibiotic resistance or the ability to use certain nutritional sources of energy) and may be tolerated by their host organisms for as long as this advantageous relationship may exist.

Genetically engineered plasmids may comprise a patchwork of genes, regulatory elements and/or structural pieces of interest. Since there are so many naturally occurring (and previously engineered) plasmids available, there is a wide choice of genes to choose from. In the case of the plasmid shown in FIGS. 1 and 2, the genes employed may be selected based on the desired properties of the finished construct. These properties may include the ability to transform the full range of useful host organisms, provide some selective advantage to the host organism (e.g., antibiotic resistance), produce a thermostable and rapidly detectable signal on demand, and provide for the signal to be off until it is desired to turn it on. This may be accomplished by piecing together (ligation) the required attributes in the form of DNA segments from a variety of source plasmids. For example, the fragments may comprise origins of replication for both gram positive and gram negative organisms, a cat gene for chloramphenicol resistance, a bgaB gene for thermostable β-galactosidase, and an xylR regulator to regulate the bgaB gene product until needed.

A plasmid of specific design may be constructed by assembling the desired genetic elements. The genetic elements may be assembled by restriction digest of the desired genetic sequence from a donor plasmid or organism to produce ends of the DNA which may then be readily ligated to another genetic sequence. Typically, a 5' or 3' overhang may be produced via restriction digest on both sequences targeted for ligation. Following digestion, the target sequences may be purified and then ligated together with an enzyme (ligase). The plasmid depicted in FIG. 3 may be constructed by assembling a base plasmid containing the origins of replication for both gram positive and gram negative organisms as well as the cat gene for chloramphenicol resistance. The xylR regulator segment may be attached to the base plasmid by restriction digest of the base plasmid and ligation of the xylR segment. Following confirmation of the proper attachment of the xylR regulator segment to the base segment, the process may be repeated for both the bgaB gene segment and the terminators T1 and T2 for this gene. Upon complete assembly of the genetic elements and confirmation of proper assembly and orientation, the plasmid may be inserted into a host organism which may be used as the test organism.

A complete virus particle, which may be referred to as a virion, may be a gene transporter that may comprise nucleic acid surrounded by a protective coat of protein which may be referred to as a capsid. A capsid may comprise proteins encoded by the viral genome and its shape may serve as a basis for morphological distinction. Virally coded protein units, which may be referred to as promoters, may self-assemble to form the capsid, requiring no input from the virus genome; however, a few viruses may code for proteins which may assist the construction of their capsid. Proteins associated with nucleic acid may be more technically known as nucleoproteins, and the association of viral capsid proteins with viral nucleic acid may be referred to as a nucleocapsid. The viruses may not be considered to be living organisms and may lack the means for self-reproduction outside a host cell. The viruses used herein with bacteria may be referred to as bacteriophages or phages. Examples of the viruses may include lambda or M13 bacteriophages. The reporter gene and the repressor gene may be inserted in the virus by first cleaving the non-recombinant phage DNA with an endonuclease and then ligating a piece of DNA to the two newly formed ends.

The vehicle (i.e., plasmid, virus) may be taken up by the test organism by: transformation or conjugation, for example, with plasmids, or transduction or transfection, for example, with viruses.

The indicator enzymes, which may be produced by the reporter gene, may comprise beta-D-galactosidase, beta-D-glucosidase, alpha-D-glucosidase, alkaline phosphatase, acid phosphatase, butyrate esterase, caprylate esterase lipase, myristate lipase, leucine aminopeptidase, valine aminopeptidase, chymotrypsin, phosphohydrolase, alpha-D-galactosidase, alpha-L-arabinofuranosidase, N-acetyl-beta-glucosaminidase, beta-D-cellobiosidase, alanine aminopeptidase, proline aminopeptidase, tyrosine aminopeptidase, phenylalanine aminopeptidase, beta-D-glucuronidase, fatty acid esterase, or a mixture of two or more thereof. Thermostable counterparts of these may be used.

The genetically engineered biological indicator may be exposed to the sterilization medium during a sterilization process using any suitable procedure. These may include use of the sterilization indicators exemplified by, but not limited to, those illustrated in FIGS. 5-7. Referring to FIGS. 5 and 6, sterilization indicator 10 may comprise carrier 12, the carrier 12 having a first surface 14 and a second surface 16; support 20, the support 20 having a first section 22 and a second section 24, the carrier 12 overlying the first section 22 of the support 20, the second surface 16 of the carrier 12 being adhered to the first section 22 of the support 20; and genetically engineered biological indicator 30 supported by the carrier 12. The biological indicator 30 may be supported by or adhered to the first surface 14 of the carrier 12. The second section 24 of the support 20 may be of sufficient dimension to permit handling the sterilization indicator 10 without contacting the biological indicator 30. That is, the second section 24 may be of sufficient dimension to function as a handle thereby permitting facilitated aseptic handling of the sterilization indicator 10.

The carrier 12 may be in the form of a relatively flat substrate which is depicted in the drawings as being in the form of a circle. However, it is to be understood that the carrier 12 may have any desired shape or form, for example, square, rectangle, oval, and the like. The carrier 12 may have a prismatic cross-section. The carrier 12 may have a thickness that is relatively small, for example, from about 0.001 to about 3 mm, and in one embodiment from about 0.01 to about 2 mm, and in one embodiment from about 0.05 to about 1.5 mm, and in one embodiment from about 0.1 to about 1 mm. The area of the first surface 14 of the carrier 12, which provides support for the biological indicator 30, may be relatively small, for example, the area may be in the range from about 1 to about 80 mm$^2$, and in one embodiment from about 2 to about 70 mm$^2$, and in one embodiment from about 3 to about 60 mm$^2$, and in one embodiment from about 5 to about 50 mm$^2$. An advantage of such a small area is that the size of the biological indicator 30 may be relatively small, and consequently the amount of recovery medium needed to incubate the biological indicator may be relatively small and the time requirement for incubation may be relatively short.

The carrier 12 may comprise a porous material or a non-porous material. The carrier may comprise a solid carrier. The carrier may comprise any material that does not dissolve or deteriorate during the sterilization or incubation processes. The carrier 12 may comprise paper, metal, glass, ceramics, plastic, membranes, or a combination of two or more thereof. The metal may comprise aluminum or steel. The plastic may comprise a polyolefin, polystyrene, polycarbonate, polymethacrylate, polyacrylamide, polyimide, polyester, and the like. The carrier 12 may comprise a film. The carrier may be in the form of a spun or unwoven felt. The carrier may comprise a mat of compressed fibers. The carrier may comprise a porous material made of sintered glass, glass fibers, ceramic, synthetic polymer, or a combination of two or more thereof. The carrier may comprise filter paper or absorbent paper. The carrier may comprise a cellulose pad.

The support 20 may comprise any material that does not dissolve or disintegrate during the sterilization or incubation processes. The support may comprise metal, glass, ceramic, plastic, or a combination thereof. The support may comprise aluminum or stainless steel. The support may comprise polystyrene, polyolefin (e.g., polypropylene, polyethylene), and the like. The support 20 may be flexible or rigid. The support 20 may be foldable. The support 20 depicted in the drawings is rectangular in shape, however, it is to be understood that the support may have any desired shape or form, for example, square, circle, oval, and the like. The length of the support 20 may be in the range from about 0.2 to about 12 cm, and in one embodiment from about 0.2 to about 10 cm, and in one embodiment from about 0.5 to about 7 cm, and in one embodiment from about 1 to about 5 cm, and in one embodiment from about 1.5 to about 3.5 cm. The width of the support 20 may be in the range from about 0.2 to about 2 cm, and in one embodiment from about 0.2 to about 1.5 cm, and in one embodiment from about 0.25 to about 1 cm. The thickness of the support 20 may be in the range from about 0.02 to about 3 mm, and in one embodiment from about 0.1 to about 2 mm. The length of the second section 24 may be in the range from about 0.2 to about 12 cm, and in one embodiment from about 0.3 to about 11 cm, and in one embodiment from about 0.5 to about 10 cm, and in one embodiment from about 1 to about 7 cm, and in one embodiment from about 1.5 to about 4.5 cm.

The support 20 may be in the form of a rectangular sheet or strip, the first section 22 of the support 20 comprising a minor part of the length of the carrier 20, the second section 24 of the support 20 comprising a major part of the length of the support 20. The ratio of the length of the second section 24 to the length of the first section 22 may be in the range from about 2:1 to about 12:1, and in one embodiment from about 4:1 to about 8:1, and in one embodiment from about 5.5:1 to about 6.5:1.

The carrier 12 may be attached to the support 20 using sonic welding, heat sealing, an adhesive, or lamination. The carrier 12 may be attached to the support 20 prior to or subsequent to applying the biological indicator 30 to the carrier 12. The carrier 12 may be attached to the support 20 subsequent to applying the biological indicator 30 to the support 12 using sonic welding or an adhesive. Sonic welding may involve frictional binding of the support to the carrier. The adhesive may be any adhesive that is compatible with the carrier 12 and the support 20, and does not dissolve or deteriorate during the sterilization or incubation processes. The adhesive should not be lethal or inhibitory to the organisms of interest. The adhesive may be a pressure sensitive adhesive.

The sterilization indicator 10 for supporting the disclosed biological indicator may be used in any process wherein the sterilization indicator is exposed to a sterilization medium during a sterilization process and then to an inducer and an enzyme substrate to determine whether the sterilization process is effective. The sterilization process may employ gaseous or liquid sterilants, dry heat, radiation, and the like. The sterilization indicator 10 along with the articles to be sterilized may be exposed to a sterilization medium during the sterilization process. Upon completion of the sterilization process, the sterilization indicator 10 may be placed in a vial containing a recovery medium comprising at least one inducer and at least one enzyme substrate. The genetically engineered biological indicator may then be incubated for a desired period of time and examined to determine whether the sterilization process was effective.

The genetically engineered biological indicator may be used in a self-contained sterilization indicator comprising a container with two separate compartments. One of the compartments may contain the biological indicator. The other compartment may contain a recovery medium comprising at least one inducer and at least one enzyme substrate. In use, the sterilization indicator and the articles to be sterilized may be exposed to the sterilization medium. Following sterilization, the sterilization indicator may be activated so that the biological indicator comes into contact with the recovery medium sufficiently to determine whether the sterilization process was effective. These sterilization indicators may be used with any sterilization process wherein the biological indicator may be exposed to the sterilization medium, for example, sterilization processes employing gaseous sterilants.

The self-contained sterilization indicator may be in the form exemplified by, but not limited to, that depicted in FIG. 7. Referring to FIG. 7, the sterilization indicator 40 may comprise tapered tube 42, inner compartment 44, and closure cap 46. The closure cap 46 includes projections 48. An annular space 43 is formed between the inner surface of tapered tube 42 and the outer surface of the inner compartment 44, the annular space 43 forming another interior compartment. The carrier 50 is positioned in the annular space 43. The genetically engineered biological indicator may be supported by the carrier 50. The carrier 50 may comprise the sterilization indicator 10 illustrated in FIGS. 4 and 5. The recovery medium may be contained in the inner compartment 44. The tapered tube 42 and the closure cap 46 may be made from any material that is compatible with the conditions and chemistries used in the sterilization process. These materials may include polycarbonate, polyolefins, polyamide, polymethacrylates, polymethylpentenes, polyesters, and the like. The inner compartment 44 may be in the form of a glass or frangible glass ampoule. Further details on the construction of tapered tube 42, inner compartment 44 and closure cap 46 may be found in U.S. Pat. No. 4,304,869, which is incorporated herein by reference. The carrier 50 may comprise a porous material or a non-porous material. The carrier 50 may comprise any material that does not dissolve or deteriorate during the sterilization or incubation processes. The carrier 50 may comprise paper, metal, glass, ceramics, plastic, membranes, or a combination of two or more thereof. The metal may comprise aluminum or steel. The plastic may comprise a polyolefin, polystyrene, polycarbonate, polymethacrylate, polyacrylamide, polyimide, polyester, and the like. The carrier 50 may comprise a film. The carrier 50 may be in the form of a spun or unwoven felt. The carrier 50 may comprise a mat of compressed fibers. The carrier 50 may comprise a porous material made of sintered glass, glass fibers, ceramic, synthetic polymer, or a combination of two or more thereof. The carrier 50 may comprise filter paper or absorbent paper. The carrier 50 may comprise a cellulose pad. During sterilization, the sterilization indicator 40, along with the articles to be sterilized are exposed to the sterilization medium. When sterilization has been completed, the closure cap 46 is pressed downwardly into the tapered tube 42. The projections 48 press against the inner compartment 44 and cause it to rupture. This allows the recovery medium to contact the carrier 50 and any of the biological indicator supported by the carrier 50 that may have survived the sterilization. After a predetermined time, the carrier 50 may be removed and the extent of sterilization may be determined by detecting change in the biological indicator.

The carrier 12 or the carrier 50 may have a surface area for supporting the genetically engineered biological indicator in the range from about 1 to about 80 mm 2, and in one embodiment in the range from about 5 to about 50 $mm^2$. The number of colony forming units (cfu) of the biological indicator supported by the carrier 12 or the carrier 50, before sterilization, may be in the range from about $10^4$ to about $10^7$ $cfu/mm^2$, and in one embodiment in the range from about $10^5$ to about $10^6$ $cfu/mm^2$.

The inducer may comprise one or more of xylose, allolactose, isopropyl thiogalactoside, metalothionine, or a mixture of two or more thereof. The inducer may be combined with the enzyme substrate in the recovery medium.

The enzyme substrate may comprise a substance or mixture of substances which when acted upon by the indicator enzyme is converted into an enzyme-modified product. In general, the enzyme-modified product may comprise a luminescent, fluorescent, or colored material. Alternatively, the enzyme substrate may comprise one or more compounds which when acted upon by the enzyme, may yield a product which reacts with an additional compound or composition to yield a luminescent, fluorescent, or colored material.

There are two basic types of enzyme substrates that may be used for the detection of specific indicator enzymes. The first type of enzyme substrate may be either fluorogenic or chromogenic, and may be given a chemical formula such as, AB. When acted upon by the indicator enzyme, AB, may break down to A+B. B, for example, may be either fluorescent or colored. In one embodiment, two B compounds may react together to produce the fluorescent or colored signal. A specific example of a fluorogenic substrate of this type may be 4-methylumbelliferyl phosphate. In the presence of the indicator enzyme phosphatase, the substrate may be broken down into 4-methylumbelliferone and phosphate. Other fluorogenic substrates of this type may include the derivatives of 4-methylumbelliferyl, 7-amido-4-methylcoumarin, indoxyl and fluorescein. An example of a chromogenic substrate of this type may be 5-bromo-4-chloro-3-indolyl phosphate. In the presence of phosphatase, the substrate may be broken down into indigo blue and phosphate. Other chromogenic substrates of this type may include derivatives of 5-bromo-4-chloro-3-indolyl, nitrophenol and phenolphthalein.

The second type of enzyme substrate may be given by the chemical formula CD, for example, which may be converted by a specific enzyme to C+D. However, neither C nor D may be fluorescent or colored, but D may be capable of being further reacted with compound Z to give a fluorescent or colored compound, thus indicating enzyme activity. A specific fluorogenic example of this type may be the amino acid lysine. In the presence of the enzyme lysine decarboxylase, lysine may lose a molecule of $CO_2$. The remaining part of the lysine may then be called cadaverine, which is strongly basic. A basic indicator such as 4-methylumbelliferone may be incorporated and may be fluoresce in the presence of a strong base. A chromogenic substrate of this type may be 2-naphthyl phosphate. The indicator enzyme phosphatase, may react with the enzyme substrate to yield beta-naphthol. The liberated beta-naphthol may react with a chromogenic reagent containing 1-diazo-4-benzoylamino-2,5-diethoxybenzene to produce a violet color.

The enzyme substrate may comprise a fluorogenic compound, defined herein as a compound capable of being enzymatically modified, e.g., by hydrolysis, to provide a derivative fluorophor which has an appreciably modified or increased fluorescence.

The fluorogenic compounds may in themselves be either non-fluorescent or meta-fluorescent (i.e., fluorescent in a distinctly different way, e.g., either by color or intensity, than the corresponding enzyme-modified products) and appropriate wavelengths of excitation and detection, may be used to separate the fluorescence signal developed by the enzyme modification from any other fluorescence that may be present.

A number of enzyme substrates for indicator enzymes of diverse origins may be used. These may include fluorogenic 4-methylumbelliferyl derivatives (hydrolyzable to 4-methylumbelliferone); derivatives of 7-amido-4-methylcoumarin; diacetylfluorescein derivatives; and fluorescamine.

Derivatives of 4-methylumbelliferyl that may be used as the enzyme substrate may include: 4-methylumbelliferyl-2-acetamido-4,6-O-benzylidene-2-deoxy-beta-D-lucopyranoside; 4-methylumbelliferyl acetate; 4-methylumbelliferyl-N-acetyl-beta-D-galactosaminide; 4-methylumbelliferyl-N-acetyl-alpha-D-glucosaminide; 4-methylumbelliferyl-N-acetyl-beta-D-glucosaminide; 2'-(4-methylumbelliferyl)-alpha-D-N-acetyl neuraminic acid; 4-methylumbelliferyl-alpha-L-arabinofuranoside; 4-methylumbelliferyl alpha-L-arabinoside; 4-methylumbelliferyl butyrate; 4-methylumbelliferyl-beta-D-cellobioside; methylumbelliferyl-beta-D-N,N'-diacetyl chitobioside; 4-methylumbelliferyl elaidate; 4-methylumbelliferyl-beta-D-fucoside; 4-methylumbelliferyl-alpha-L-fucoside; 4-methylumbelliferyl-beta-L-fucoside; 4-methylumbelliferyl-alpha-D-galactoside; 4-methylumbelliferyl-beta-D-galactoside; 4-trifluoromethylumbelliferyl beta-D-galactoside; 6,8-difluoro-4-methylumbelliferyl-beta-D-galactoside; 4-methylumbelliferyl-alpha-D-glucoside; 4-methylumbelliferyl-beta-D-glucoside; 4-methylumbelliferyl-7,6-sulfo-2-acetamido-2-deoxy-beta-D-glucoside; 4-methylumbelliferyl-beta-D-glucuronide; 6,8-difluor-4-methylumbelliferyl-beta-D-glucuronide; 4-methylumbelliferyl p-guanidinobenzoate; 4-methylumbelliferyl heptanoate; 4-methylumbelliferyl-alpha-D-mannopyranoside; 4-methylumbelliferyl-beta-D-mannopyranoside; 4-methylumbelliferyl oleate; 4-trifluoromethylumbelliferyl oleate; 4-methylumbelliferyl palmitate; 4-methylumbelliferyl phosphate; 4-methylumbelliferyl propionate; 4-methylumbelliferyl stearate; 4-methylumbelliferyl sulfate; 4-methylumbelliferyl-beta-D-N,N',N"-triacetylchitotriose; 4'-methylumbelliferyl 2,3,5-tri-beta-benzoyl-alpha-L-arabinofuranoside; 4-methylumbelliferyl-beta-trimethylammonium cinnamate chloride; 4-methylumbelliferyl 4-guanidinobenzoate; and 4-methylumbelliferyl-beta-D-xyloside.

Derivatives of 7-amido-4-methylcoumarin that may be used as the enzyme substrate may include: L-alanine-7-amido-4-methylcoumarin; L-proline-7-amido-4-methylcoumarin; L-tyrosine-7-amido-4-methylcoumarin; L-arginine-7-amido-4-methylcoumarin; L-citrulline-7-amido-4-methylcoumarin; L-leucine-7-amido-4-methylcoumarin; L-methionine-7-amido-4-methylcoumarin; L-pyroglutamic acid 7-amido-4-methylcoumarin; L-aspartic acid beta-(7-amido-4-methylcoumarin); L-glutamic acid 1-(7-amido-4-methylcoumarin); L-phenylalanine-7-amido-4-methylcoumarin; and 7-glutaryl-phenylalanine-7-amido-4-methylcoumarin.

Peptide derivatives of 7-amido-4-methyl coumarin that may be used as the enzyme substrate may include: N-t-BOC-Ile-Glu-Gly-Arg 7-amido-4-methylcoumarin; N-t-BOC-Leu-Ser-Thr-Arg 7-amido-4-methylcoumarin; N-CBZ-Phe-Arg 7-amido-4-methylcoumarin; N-succinyl-Leu-Tyr-7-amido-4-methylcoumarin; Gly-Pro 7-amido-4-methylcoumarin; Pro-Phe-Arg 7-amido-4-methylcoumarin; N-t-BOC-Val-Pro-Arg 7-amido-4-methylcoumarin; and N-glutaryl-Gly-Arg 7-amido-4-methylcoumarin.

Derivatives of diacetylfluorescein that may be used as the enzyme substrate may include fluorescein diacetate, fluorescein dibutyrate, 2',7'-dichlorofluorescein diacetate, fluorescein di-(beta-D-N-acetygalactosamine), fluorescein di-(beta-D-galactoside), fluorescein mono-(beta-D-galactoside), and fluorescein dilaurate.

Where the indicator enzyme whose activity is to be detected is alpha-D-glucosidase, chymotrypsin or fatty acid esterase, a fluorogenic enzyme substrate that may be used may be 4-methylumbelliferyl-alpha-D-glucoside, 7-glutarylphenylalanine-7-amido-4-methyl coumarin, or 4-methylumbelliferyl heptanoate, respectively. Where the indicator enzyme whose activity is to be detected is alpha-L-arabinofuranosidase, a fluorogenic enzyme substrate that may be used may be 4-methylumbelliferyl-alpha-L-arabinofuranoside. Where the indicator enzyme whose activity is to be detected is beta-D-glucosidase, a fluorogenic enzyme substrate that may be used may be 4-methylumbelliferyl-beta-D-glucoside.

An enzyme substrate that may be used may be a chromogenic compound capable of being enzymatically modified to give a derivative chromophor, or a product which reacts with another compound to give a derivative chromophor, which chromophor has a different or more intense color. The chromogenic compounds may be non-colored or colored in a distinctly different way, e.g., either by color or intensity, than the corresponding enzyme-modified products. Appropriate wavelengths of excitation and detection, in manners well known to users of colorometric instrumentation, may be used to separate the colored signal developed by the enzyme modification from any other color that may be present.

Chromogenic compounds that may be used as enzyme substrates may include 5-bromo-4-chloro-3-indolyl derivatives; nitrophenyl derivatives; indoxyl derivatives; and phenolphthalein derivatives.

Derivatives of 5-bromo-4-chloro-3-indolyl that may be used may include 5-bromo-6-chloro-3-indolyl acetate, 5-bromo-4-chloro-3-indolyl acetate, 5-bromo-4-chloro-3-indoxyl-beta-D-galactopyranoside, 5-bromo-4-chloro-3-indolyl-1,3-diacetate, 5-bromo-4-chloro-3-indolyl-beta-D-fucopyranoside, 5-bromo-4-chloro-3-indolyl-beta-D-glucopyranoside, 5-bromo-4-chloro-3-indolyl-beta-D-glucuronic acid, 5-bromo-4-chloro-3-indolyl phosphate, and 5-bromo-4-chloro-3-indolyl sulfate.

Derivatives of nitrophenyl that may be used may include p-nitrophenol and o-nitrophenol derivatives. These include diethyl-p-nitrophenyl phosphate; di-p-nitrophenyl phosphate; p-nitrophenyl-2-acetamido-2-deoxy-3-O-beta-galactopyranosyl-beta-glucopyranoside; p-nitrophenyl-2-acetamido-2-deoxy-beta-glucopyranoside; p-nitrophenyl acetate; p-nitrophenyl-N-acetyl-beta-D-glucosaminide; p-nitrophenyl-beta-D-N,N'-diacetylchitobioside; p-nitrophenyl-alpha-glucopyranoside; p-nitrophenyl-alpha-maltoside; p-nitrophenyl-beta-maltoside; p-nitrophenyl-alpha-mannopyranoside; p-nitrophenyl-beta-mannopyranoside; p-nitrophenyl myristate; p-nitrophenyl palmitate; p-nitrophenyl phosphate; bis(p-nitrophenyl)phosphate; tris(p-nitrophenyl)phosphate; p-nitrophenyl-beta-glucopyranoside; p-nitrophenyl-beta-glucuronide; alpha-p-nitrophenylglycerine; p-nitrophenyl-alpha-rhamnopyranoside; p-nitrophenyl stearate; p-nitrophenyl sulfate; p-nitrophenyl-2,3,4,6-tetra-O-acetyl-beta-glucosaminide; p-nitrophenyl thymidine monophosphate; p-nitrophenyl-2,3,4-tri-O-acetyl-beta-glucuronic acid methyl ester; and p-nitrophenyl valerate.

Useful o-nitrophenols may include o-nitrophenyl acetate, o-nitrophenyl-beta-glucoside and o-nitrophenyl-beta-D-glucopyranoside. Other useful nitrophenyl derivatives may include nitrophenyl-beta-fucopyranoside; nitrophenyl-alpha-galactopyranoside; nitrophenyl-beta-galactopyranoside; nitrophenyl butyrate; nitrophenyl caprate; nitrophenyl caproate; nitrophenyl caprylate; nitrophenyl laurate; and nitrophenyl propionate.

Indoxyl derivatives that may be used may include indoxyl-acetate; indoxyl beta-D-glucoside; 3-indoxyl sulfate; and 3-indoxyl phosphate.

Phenolphthalein derivatives that may be used may include: phenolphthalein dibutyrate; phenolphthalein diphosphate; phenolphthalein disulfate; phenolphthalein glucuronic acid; phenolphthalein mono-beta-glucosiduronic acid; phenolphthalein mono-beta-glucuronic acid; and phenolphthalein mono-phosphate.

The above-described chromogenic enzyme substrates may react directly with an appropriate indicator enzyme to produce a chromophor.

Additional enzyme substrates containing 1-naphthyl, 2-naphthyl and Napthyl-AS-BI derivatives may be employed if the derivative enzyme modified product is further reacted with a chromogenic reagent, such as diazotized dyes, e.g., 1-diazo-4-benzoylamino-2,5-diethoxybenzene, 1-diazo-4-benzoylamino-2,5-diethoxybenzene, p-diazo-2,5-diethoxy-N-benzoyalanine, 4-chloro-2-methylbenzene diazonium chloride, and o-aminoazotoluene diazonium salt, to produce a chromophor.

Derivatives of 1-napthyl that may be used may include 1-naphthyl-N-acetyl-beta-D-glucosaminide.

Derivatives of 2-naphthyl that may be used may include 2-naphthyl-phosphate; 2-naphthyl-butyrate; 2-naphthyl-caprylate; 2-naphthyl-myristate; L-leucyl-2-naphthylamide; L-valyl-2-naphthylamide; L-cystyl-2-naphthylamide; N-benzoyl-DL-arginine-2-naphthylamide; N-glutaryl-phenylalanine 2-naphthyl-amine; 2-naphthyl-phosphate; 6-Br-2-naphthyl-alpha-D-galacto-pyranoside; 2-naphthyl-beta-D-galacto-pyranoside; 2-naphthyl-2-D-glucopyranoside; 6-bromo-2-naphthol-beta-D-glucopyranoside; 6-bromo-2-naphthyl-2-D-mannopyranoside; and 2-naphthyl-alpha-L-fucopyranoside.

Derivatives of naphthyl-AS-BI that may be used may include naphthyl-AS-BI-phosphate; and naphthyl-AS-BI-beta-D-glucuronide.

Where the indicator enzyme whose activity is to be detected is alpha-D-glucosidase, the enzyme substrate may be p-nitrophenyl-alpha-glucopyranoside. Where the indicator enzyme whose activity is to be detected is alpha-L-arabinofuranosidase, the enzyme substrate that may be used may be p-nitrophenyl-alpha-L-arabinofuranoside. Where the indicator enzyme whose activity is to be detected is β-galactosidase, the enzyme substrate may be 5-bromo-4-chloro-3-indolyl-β-D-galactopyranoside or 4-methylumbelliferone-β-D-galactopyranoside.

The enzyme substrate that may be used may depend upon the identity of the indicator enzyme whose activity is under study. Below is a list of a number of enzyme substrates and corresponding indicator enzymes which may react with the enzyme substrate to produce a product having appreciably modified or increased fluorescence or color.

| Enzyme Substrate | Indicator Enzyme |
|---|---|
| 4-Methylumbelliferyl acetate | Esterase |
| 4-Methylumbelliferyl butyrate | Esterase |
| 4-Methylumbelliferyl elaidate | Lipase |
| 4-Methylumbelliferyl-β-D-galactopyranoside | β-D-Galactosidase |
| 4-Methylumbelliferyl-α-D-galactopyranoside | α-D-Galactosidase |
| 4-Methylumbelliferyl-α-D-glucopyranoside | α-D-Glucosidase |
| 4-Methylumbelliferyl-β-D-glucopyranoside | β-D-Glucosidase |
| 4-Methylumbelliferyl heptanoate | Esterase |
| 4-Methylumbelliferyl oleate | Lipase |
| 4-Methylumbelliferyl phosphate | Acid or Alkaline Phosphatase |
| 4-Methylumbelliferyl propionate | Esterase |
| 4-Methylumbelliferyl-β-D-galactoside | β-D-Galactosidase |
| 4-Methylumbelliferyl-β-D-glucoside | β-D-Glucosidase |
| 4-Methylumbelliferyl-α-D-glucoside | α-D-Glucosidase |
| 4-Methylumbelliferyl-α-L-arabinofuranoside | α-L-Arabinofuranosidase |
| L-Leucine-7-amido-4-methylcoumarin | Leucine aminopeptidase |
| 7-glutaryl-phenylalanine-7-amido-4-methylcoumarin | Chymotrypsin |
| D-Melibiose | α-D-Galactosidase |
| p-Nitrophenyl phosphate | Alkaline or Acid phosphatase |
| p-Nitrophenyl acetate | Lipase |
| o-Nitrophenyl-β-D-galactopyranoside | β-D-Galactosidase |
| p-Nitrophenyl-α-D-galactopyranoside | α-D-Galactosidase |
| o-Nitrophenyl-β-D-glucopyranoside | β-D-Glucosidase |
| p-Nitrophenyl-α-D-glucopyranoside | α-D-Glucosidase |
| p-Nitrophenyl-β-D-glucuronide | β-D-Glucuronidase |
| p-Nitrophenyl-α-L-arabinofuranoside | α-L-Arabinofuranosidase |
| p-Nitrophenyl laurate | Esterase |
| p-Nitrophenyl myristate | Esterase |
| p-Nitrophenyl palmitate | Esterase |
| p-Nitrophenyl phosphate diNa salt | Alkaline Phosphatase |
| Phenolphthalein dibutyrate | Esterase |
| Phenolphthalein diphosphate | Acid or Alkaline phosphatase |
| Phenolphthalein diphosphate pentaNa salt | Acid or Alkaline phosphatase |
| Phenolphthalein-β-D-glucuronide Na salt | β-D-Glucuronidase |
| Phenolphthalein-β-D-glucuronide | β-D-Glucuronidase |
| L-Phenylalanine ethylester HCl | Chymotrypsin |
| Phenyl-β-D-galactopyranoside | β-D-Galactosidase |
| Phenyl-β-D-glucuronide | β-D-Glucuronidase |
| Phenyl-β-D-glucopyranoside | β-D-Glucosidase |
| Phenyl-β-D-glucuronide | β-D-Glucuronidase |
| Phenyl-α-D-glucoside | α-D-Glucosidase |
| Sodium β-glycerophosphate | Acid or Alkaline phosphatase |

| Enzyme Substrate | Indicator Enzyme |
|---|---|
| Sodium 1-naphthyl phosphate | Acid or Alkaline phosphatase |
| Sodium 2-naphthyl phosphate | Acid or Alkaline phosphatase |
| 2-Naphthyl-butyrate | Esterase |
| β-Naphthyl acetate | Lipase |
| 6-Br-2-naphthyl-β-D-glucoside | β-D-Glucosidase |
| L-Leucyl-2-naphthylamide aminopeptidase | Leucine |
| L-Valyl-2-naphthylamide aminopeptidase | Valine |
| N-glutaryl-phenylalanine-2-naphthylamine | Chymotrypsin |
| Naphthyl-AS-BI-PhosPhate | Phosphohydralase |
| Indoxyl acetate | Lipase |
| N-Methylinodoxyl acetate | Lipase |
| N-Methylinodoxyl myristate | Lipase |
| 5-Bromoindoxyl acetate | Lipase |
| 3-Indoxyl phosphate | Acid or Alkaline phosphatase |
| Indoxyl-β-D-glucoside | β-D-Glucosidase |
| 5-Br-4-Cl-3-Indolyl acetate | Lipase |
| 5-Br-4-Cl-3-Indolyl phosphate | Alkaline or Acid phosphatase |
| 5-Br-4-Cl-3-Indolyl-β-D-glucuronic acid | β-D-Glucuronidase |
| Diacetylfluorescein | Lipase/esterase |

Where the indicator enzyme is β-galactosidase, the enzyme substrate may comprise 5-Bromo-4-chloro-3-indolyl-β-D-galactopyranoside (X-gal), 5-Bromo-6-chloro-3-indolyl-α-galactopyranoside (Mag-gal), 5-Bromo-3-indolyl-β3-D-galactopyranoside (Bluo-gal), 6-Bromo-2-naphthyl-β-D-galactopyranoside, 6-chloro-3-indolyl-β-D-galacotpyranoside (Rose-gal), 3-Indoxyl-β-D-galactopyranoside (Y-gal), 5-Iodo-3-indoxyl-β-D-galactopyranoside, N-methylindoxyl-β-D-galactopyranoside, 2-Nitrophenyl-β-D-galactopyranoside (ONPG), 4-Nitrophenyl-β-D-galactopyranoside (PNPG), Phenyl-β-D-galactopranoside (P-gal), 2-Chloro-4-nitrophenyl-β-D-lactoside, 4-methylumbelliferyl-β-D-galactopyranoside, 4-trifluoromethylumbelliferyl-β-D-galactopyranoside, Fluorescein di(β-D-galactopyranoside) (FDG), Fluorescein mono-β-D-galactopyranoside, Fluorescein di-(β-D-acetyl galactosamine), 4-Methylumbelliferyl-β-D-lactopyranoside, 2-Napthyl-β-D-galactopyranoside, 8-Hydroxyquinoline-β-D-galactopyranoside, Resorufin β-D-galactopyranoside, 3-Carboxyumbelliferyl-β-D-galactopyranoside, 4-Chloromethyl-6,8-difluoroumbelliferyl-β-D-galactopyranoside, 6,8-Difluor-4-methylumbelliferyl-β-D-galactopyranoside, 6,8-Difluoro-4-heptadecylumbelliferyl-β-D-galactopyranoside, 5-(Pentafluorobenzoylamino)-fluorescein-β-D-galactopyranoside, $C_2$-fluorescein-β-D-galactopyranoside, $C_8$-fluorescein-β-D-galactopyranoside, $C_{12}$-fluorescein-β-D-galactopyranoside, 5-Chloromethylfluorescein-β-D-galactopyranoside, $C_{12}$-resorufin-β-D-galactopyranoside, 7-Hydroxyl-9H-(1,3-dichlor-9,9-dimethylacridin-2-one) (DDAO), or a mixture of two or more thereof.

After the sterilization process has been completed, the carrier 12 or the carrier 50, with any of the genetically engineered biological indicators that may have survived the sterilization process on it, may be contacted with or placed in a recovery medium containing a nutrient growth media, an inducer and an enzyme substrate. The recovery medium may comprise an aqueous medium or aqueous solution that provides for germination, metabolism and subsequent grow out of organisms as required. The aqueous medium or aqueous solution may be buffered. The inducer may cause the repressor gene in the biological indicator to dissociate from the vehicle (i.e., plasmid, virus). This may allow transcription/translation to occur thus producing the indicator enzyme. The indicator enzyme may contact the enzyme substrate resulting in the formation of the enzyme-modified product which may have a detectable color or fluorescence.

The concentration of enzyme substrate in the aqueous solution or aqueous medium may be dependent upon the identity of the enzyme substrate and the indicator enzyme, the amount of enzyme-modified product that must be generated to be detectable, either visually or by instrument, and the amount of time required to determine whether indictor enzyme is present. The amount of enzyme substrate that may be sufficient may be the amount needed to react with any indicator enzyme that may be present after the sterilization has been completed such that an enzyme-modified product at a molar concentration of at least about $10^{-15}$ molar may be produced within a period of up to about 4 hours, and in one embodiment a molar concentration of at least about $10^{-8}$ molar within a period up to about 2 hours.

The concentration of inducer in the aqueous solution or aqueous medium may be in the range from about 1 to about 20% w/v, and in one embodiment in the range from about 1 to about 5% by w/v, and in one embodiment about 2% w/v.

The pH of the aqueous solution aqueous medium containing the nutrient growth media, inducer and enzyme substrate may be in the range from about 5 to about 9.5, and in one embodiment about 7.5.

The inducer and the enzyme substrate in the recovery medium may be incubated with the biological indicator after the biological indicator has been subjected to the sterilization cycle. Incubation may be continued for a period of time and under conditions sufficient to liberate a detectable amount of the enzyme-modified product, assuming any of the biological indicator remains functional. In general, the amount of enzyme-modified product which may be detectable may be as low as about $1 \times 10^{-15}$ molar. The incubation conditions may be sufficient to generate at least about $1 \times 10^{-8}$ molar of enzyme-modified product, and in one embodiment from about $1 \times 10^{-6}$ to about $1 \times 10^{-5}$ molar of enzyme-modified product. The incubation time and temperature needed to produce a detectable amount of enzyme-modified product may depend upon the identity of the indicator enzyme and the enzyme substrate, and the concentrations of each present in the recovery medium. In general, the incubation temperature may be in the range from about 20° C. to about 70° C. The incubation time may be in the range up to about 4 hours, and in one embodiment in the range from about 0.01 to about 4 hours, and in one embodiment in the range from about 0.1 to about 3 hours, and in one embodiment in the range from about 0.1 to about 2 hours, and in one embodiment in the range from about 0.2 to about 1 hour.

Generally applicable methods for detecting the enzyme-modified product that may be used may include photometric, potentiometric, gravimetric, calorimetric, conductometric, or amperometric techniques. Fluorometric or spectrophotometric methods may be used. For example, the enzyme substrate may comprise a 4-methylumbelliferyl derivative which on interaction with the indicator enzyme may give rise to umbelliferone which may be monitored fluorometrically, or the substrate may comprise a nitrophenol, or similar type of derivative, which on interaction with the indicator enzyme may give rise to an enzyme-modified product which may be monitored calorimetrically.

The biological indicator, although herein described primarily in terms of a single indicator enzyme, may provide a plurality of indicator enzymes. For example, the biological indicator may provide three types of indicator enzymes, one enzyme being resistant to heat, a second being resistant to gaseous sterilizing media, and a third being resistant to radiation, e.g., gamma or beta irradiation.

The disclosed technology may provide a number of advantages over the prior art. These may include sourcing an enzyme (e.g., beta galactosidase) solely on the basis of signal generation strategy, selecting an enzyme substrate (e.g., 5-bromo-4-chloro-3-indolyl-β-D galactopyranoside or X-gal) for the enzyme that does not always necessitate the use of an electromechanical reader, and coupling sterility assurance (cell death) to the overall genetic viability of the test organism. By limiting the role of the indicator enzyme to signal generation, the need to match or correlate the susceptibility of the indicator enzyme to that of the test organism may be eliminated.

Advantages of using the disclosed genetically engineered biological indicator may include providing results of whether the sterilization is effective within a relatively short period of time in the range up to about 4 hours, and in one embodiment in the range from about 0.01 to about 4 hours, and in one embodiment in the range from about 0.1 to about 3 hours, and in one embodiment in the range from about 0.1 to about 2 hours, and in one embodiment in the range from about 0.2 to about 1 hour. By virtue of the use of the disclosed genetically engineered biological indicator, it may be possible to measure the viability of a test organism directly, rather than by indirect measurement of a surrogate molecule. The use of the disclosed biological indicator may not be limited to any particular method of sterilization. That is, the disclosed biological indicators may be used for any sterilization process. The effectiveness of a sterilization process may be determined using the disclosed genetically engineered biological indicator without requiring grow out to provide final confirmation of the effectiveness of the sterilization. By using the disclosed biological indicator, it may not be necessary to employ an electrochemical sensor to determine whether the sterilization is effective, although more rapid results with a sensor may be possible. The disclosed biological indicator may be amendable to use with instant read applications such as chip or sensor applications. The disclosed genetically engineered biological indicator may be applicable to any process employing a most resistant organism, clinically significant organism or bio-warfare organism.

The use of the disclosed genetically engineered biological indicator for detecting the effectiveness of a sterilization process may involve the use of measurement based on a genetic theory model (only a living cell can express a gene). The disclosed genetically engineered biological indicator may respond to any lethal event or combination of lethal events (transcription, translation, etc.). The disclosed biological indicator may provide a fast acting response to any biocidal mode of action (steam, peracetic acid, ethylene oxide, liquid formaldehyde, gaseous formaldehyde, stabilized liquid hydrogen peroxide, vaporous hydrogen peroxide, dry heat, ozone, ortho-phthalaldehyde, gluteraldehyde, chloramines, quaternary amines, phenolics, iodophores, ionizing radiation, ultraviolet radiation, pulsed white light, plasma, microwave radiation, etc.). The use of the disclosed genetically engineered biological indicator may provide the advantage of the absence of an indicator enzyme or reporter molecule (e.g., beta-galactosidase) prior to or during the sterilization process under evaluation.

Example 1

Figure 4:
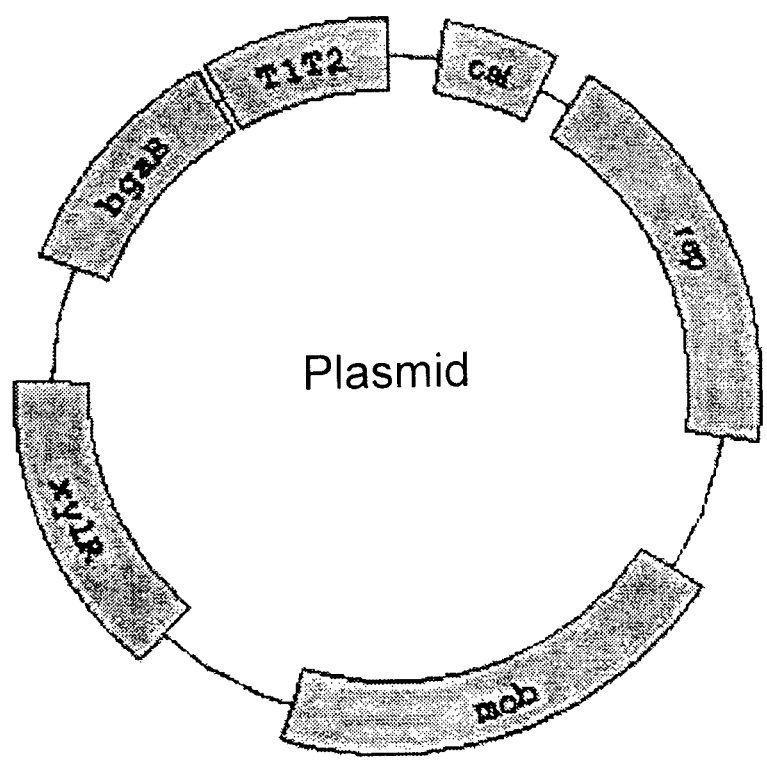
FIG. 4 is a diagram of the plasmid construct used in Example 1.

The plasmid illustrated in FIG. 4 is constructed by restriction digest of the base plasmid and ligation of the xylR regulator segment to the base plasmid. Following confirmation of the proper attachment of the xylR regulator to the base segment, the process is repeated for both the bgaB gene segment and the terminators T1 and T2 for this gene. Upon complete assembly of the genetic elements and confirmation of proper assembly and orientation, the plasmid is inserted into a host organism. The plasmid may be referred to as Plasmid No. 1.

Example 2

A plasmid may be internalized using transformation technique within a host organism using several methods. These methods may include protoplasting, electroporation, ballistic methodologies, induction of competence, transduction, or chemical (calcium chloride) methods. For this example, competent *E. coli* is transformed via chemical transformation. *E. coli* deficient of any restriction system is stored at −70° C. The *E. coli* is thawed on ice and mixed. The *E. coli* is exposed to Plasmid No. 1 on ice for 30 minutes. The resulting *E. coli*/plasmid mixture is heat shocked at 42° C. for 30 seconds and transferred to an ice bath for two minutes. Warmed media is then added to the *E. coli*/plasmid mixture and incubated at 37° C. for 60 minutes. Samples are placed on agar plates containing antibiotic and X-gal. Colonies exhibiting a blue color are successfully transformed.

Example 3

*Bacillus subtilis* is grown overnight in LB broth containing 0.5 M sorbitol, washed three times in 10% by weight glycerol with 0.5 M sorbitol and 0.5 M mannitol, and subjected to electroporation in the presence of Plasmid No. 1. Electroporation is performed over a range of voltages (1800-2500 V). The resulting organisms are recovered in media (LB broth with 0.5 M sorbitol and 0.5 M mannitol) and allowed to recover for three hours at 37° C. Following recovery, organisms are placed on LB agar plates containing antibiotic for selection of transformed organisms and allowed to incubate at 37° C. Colonies exhibiting growth are placed on LB agar plates containing an inducer (2% by weight xylose), selectable marker (chloramphenicol at 5 mg/mL), and X-gal (80 mg/mL). Colonies exhibiting a blue color on these agar plates are successfully transformed.

Transformed *Bacillus subtilis* is sporulated using the following method. An aliquot of vegetative *B. subtilis* is spread across agar media plates. The agar plates are incubated at 37° C. for five days. Following incubation, the organisms are aseptically recovered from the agar surface and evaluated for sporulation using phase contrast microscopy. The endospores are washed several times prior to use.

Example 4

Transformed *Bacillus subtilis* spores are inoculated directly onto the bottom of several SCBI vials manufactured from different materials (Lexan, Huntsman P4G4Z-011, Huntsman P4C6Z-D59, and Exxon PD9465E1 and a 200 μL microcell) and air dried overnight. A 10 μL aliquot of a $10^8$ cfu/mL spore suspension of transformed *B. subtilis* is used for inoculation. Following drying of the inoculated spore suspension and immediately prior to incubation, 1 mL of LB broth with 2% xylose is added to the Lexan, Huntsman, and Exxon materials. To the microcell, 100 μL of LB broth with 2% by weight xylose is added.

LB broth has the following formulation:

| | |
|---|---|
| Deionized water | 800 mL |
| NaCl | 10 g/l |
| Tryptone | 10 g/l |
| Yeast extract | 5 g/l |
| Xylose | 20 g/l |

Deionized water to provide final volume of 1 liter
5N NaOH to adjust pH to 7.0

Immediately following the addition of growth media, 100 μL of a 200 μg/mL 4-methylumbelliferyl-beta-D-galactoside (MUG) in N,N-dimethylformamide (DMF) are added to the samples (10 μL for the microcell). Each sample is placed in a Turner Modulus preheated in a 37° C. incubator. The Turner Modulus is operated in the UV fluorescence mode. The fluorescence produced from the enzymatic conversion of the substrate resulting from the production beta-galactosidase from the growing organisms is evaluated every minute for 3 hours. An increase in fluorescence indicates the production of beta-galactosidase. The results are as follows:

| | Incubation Time (min) | | | |
|---|---|---|---|---|
| Sample | 60 min | 90 min | 120 min | 180 |
| Lexan | 0.8716 | 0.8679 | 0.8677 | 0.8680 |
| Huntsman P4G4Z-011 | 0.8399 | 0.8386 | 0.8386 | 0.8384 |
| Huntsman P4O6Z-D59 | 0.8497 | 0.8448 | 0.8423 | 0.8428 |
| Exxon | 0.8470 | 0.8437 | 0.8425 | 0.84431 |
| Microcell | 0.8696 | 0.8697 | 0.8735 | — |

Fluorescence data is normalized.

Example 5

The amount of beta-galactosidase produced from transformed *Bacillus subtilis* grown in LB growth media with various concentrations of xylose is evaluated using a UV-vis spectrophotometer. The following combinations are evaluated:

LB broth only
LB broth containing 1% by weight xylose
LB broth containing 2% by weight xylose
LB broth containing 3% by weight xylose The following procedure is used. 9 mLs of each media-xylose combination is transferred to a sterile beaker. A 1 mL aliquot of $10^8$ cfu/mL transformed *Bacillus subtilis* spores is transferred into each beaker to give an initial starting concentration of $10^7$ cfu/mL *B. subtilis* spores. Each sample is incubated at 37° C. for 6.5 hours to allow for sufficient beta-galactosidase production to occur. Following incubation, each sample is filtered through a 0.45 μm HV Durapore filter. A 1 mL aliquot of each sample is reacted with a 1 mL aliquot of 1.0 mg/mL ONPG (in phosphate buffer) solution for 30 minutes at room temperature in a UV-vis cuvette. Absorbance measurements at 420 nm are taken of each sample. The absorbance results are as follows:

| Media | Abs at 420 nm |
|---|---|
| LB broth only | 0.002 |
| LB broth with 1% by weight xylose | 0.075 |
| LB broth with 2% by weight xylose | 0.113 |
| LB broth with 2% by weight xylose | 0.067 |

Higher absorbance values correlate to higher beta-galactosidase production.

Example 6

Samples of transformed *Bacillus subtilis* spore suspension are inoculated into 200 μL microcells to give the following spore populations: $10^6$, $10^4$, $10^2$, $10^0$ cfu/microcell. To each inoculated microcell, 100 μL of LB broth with 2% by weight xylose and 10 μL of 100 μg/mL MUG in DMF are added. Each sample is placed into the Turner Modulus at 37° C. and fluorescence measurements are taken every minute for 2 hours. An increase in fluorescence indicates production of beta-galactosidase. The results are as follows:

| | Incubation Time (min) | | | | | |
|---|---|---|---|---|---|---|
| Population | 15 | 30 | 45 | 60 | 90 | 120 |
| $10^6$ cfu | 0.8566 | 0.8465 | 0.8530 | 0.8549 | 0.8636 | 0.8708 |
| $10^4$ cfu | 0.8797 | 0.8705 | 0.8770 | 0.8751 | 0.8790 | 0.8841 |
| $10^2$ cfu | 0.8617 | 0.8516 | 0.8515 | 0.8588 | 0.8648 | 0.8699 |
| $10^0$ cfu | 0.9167 | 0.9019 | 0.9009 | 0.8977 | 0.8984 | 0.9016 |

Fluorescence data is normalized.

Example 7

A 10 μL aliquot of $10^8$ cfu/mL transformed *Bacillus subtilis* spores is transferred into each of four 200 μL microcells. The resulting inoculated microcells are air dried. To each sample, 100 μL of LB broth with 2% by weight xylose are added. Then 10 μL of the appropriate concentration of MUG are added. The following MUG concentrations are evaluated:

1.0 mg/mL

500 μg/mL

200 μg/mL

100 μg/mL

All MUG solutions contain MUG dissolved in DMF. Following addition of the MUG solutions to the microcell, the microcell is placed into the Turner Modulus and preheated to 37° C. in an incubator. Fluorescence measurements are taken every minute for 120 minutes. An increase in fluorescence indicates the production of beta-galactosidase. The results are as follows:

| MUG | Incubation Time (min) | | | | | |
|---|---|---|---|---|---|---|
| Concentration | 15 | 30 | 45 | 60 | 90 | 120 |
| 1 mg/mL | 0.9100 | 0.9003 | 0.8955 | 0.8926 | 0.8955 | 0.9003 |
| 500 µg/mL | 0.8867 | 0.8852 | 0.8935 | 0.8959 | 0.9011 | 0.9094 |
| 200 µg/mL | 0.8513 | 0.8562 | 0.8588 | 0.8602 | 0.8659 | 0.8726 |
| 100 µg/mL | 0.8643 | 0.8694 | 0.8721 | 0.8754 | 0.8807 | 0.8870 |

Fluorescence data is normalized.

While the disclosed technology has been explained in relation to specific embodiments, it is to be understood that various modifications thereof will become apparent to those skilled in the art upon reading the specification. Therefore, it is to be understood that the invention disclosed herein is intended to cover such modifications as fall within the scope of the appended claims.

The invention claimed is:

1. A genetically engineered biological indicator in a self-contained sterilization indicator, comprising:
at least one test organism and at least one reporter gene for producing an indicator enzyme, the reporter gene being taken up by the test organism, the test organism comprising bacterial spores, the reporter gene comprising bgaB; and
at least one repressor gene that inhibits expression of the reporter gene until the reporter gene is exposed to at least one inducer, the repressor gene comprising xylR;
wherein the genetically engineered biological indicator is a component of a self-contained sterilization indicator comprising a first compartment and a second compartment, the first compartment being adapted to permit the biological indicator to be brought into contact with a sterilization medium during sterilization, the second compartment containing an enzyme substrate and a growth medium for the genetically engineered biological indicator, the second compartment being adapted both to maintain the enzyme substrate and the growth medium separate from the sterilization medium during the sterilization and to permit the enzyme substrate and the growth medium to contact the biological indicator after the biological indicator has been exposed to the sterilization medium.

2. The biological indicator of claim 1 wherein the at least one reporter gene comprising bgaB and the at least one repressor gene comprising xylR are taken up by the test organism using at least one plasmid.

3. The biological indicator of claim 1 wherein the test organism comprises spores of *Geobacillus stearothermophilus, Bacillus atrophaeus, Bacillus subtilis, Bacillus sphaericus, Bacillus anthracis, Bacillus pumilus, Bacillus coagulans, Clostridium sporogenes, Clostridium difficile, Clostridium botulinum, Bacillus subtilis globigii, Bacillus cereus, Bacillus circulans* or a mixture of two or more thereof.

4. The biological indicator of claim 1 wherein an indicator enzyme is produced by the reporter gene, the indicator enzyme comprising beta-D-galactosidase.

5. The biological indicator of claim 1 wherein the test organism further comprises lacZ as a further reporter gene and an indicator enzyme is produced by the further reporter gene, the indicator enzyme comprising beta-D-galactosidase.

6. The biological indicator of claim 2 wherein the plasmid comprises a circular double-stranded DNA.

7. The biological indicator of claim 2 wherein the plasmid is linear.

8. The biological indicator of claim 2 wherein the size of the plasmid is in the range from about 2000 to about 20000 base pairs.

9. The biological indicator of claim 2 wherein from 1 to about 3000 copies of the same plasmid are taken up by a single cell of the test organism.

10. The biological indicator of claim 2 wherein the plasmid comprises one or more DNA sequences that serves as an origin of replication.

11. The biological indicator of claim 2 wherein the plasmid comprises one or more genetic markers.

12. The biological indicator of claim 2 wherein the plasmid comprises one or more multiple cloning sites.

13. The biological indicator of claim 2 wherein the plasmid comprises one or more genes that provide a selective marker to induce the test organism to retain the plasmid.

14. The biological indicator of claim 2 wherein the plasmid comprises at least one origin of replication, at least one selectable marker gene, at least one inducible promoter and the at least one reporter gene.

15. The biological indicator of claim 2 wherein the plasmid comprises two origins of replication.

16. The biological indicator of claim 2 wherein the plasmid comprises a gram negative origin of replication and a gram positive origin of replication.

17. The biological indicator of claim 16 wherein the gram negative origin of replication is from *Escherichia coli*, and the gram positive origin of replication is from *Bacillus subtilis, Geobacillus stearothermophilus, Bacillus atrophaeus*, or a mixture of two or more thereof.

18. The biological indicator of claim 2 wherein the plasmid comprises an antibiotic resistance gene and/or a gene with exogenous nutritional capability.

19. The biological indicator of claim 2 wherein the plasmid comprises a chloramphenicol, ampicillin or spectinomycin resistance gene, and/or a xylose, lactose or amino acid nutritional gene.

20. The biological indicator of claim 1 wherein the inducer comprises xylose.

21. A sterilization process, comprising:
exposing an article to be sterilized and the sterilization indicator of claim 1 to a sterilization medium.

22. The process of claim 21 wherein the sterilization medium comprises steam, dry heat, radiation, plasma, one or more gaseous sterilants and/or one or more liquid sterilants.

23. The process of claim 21 wherein the sterilization medium comprises electron beam radiation, electromagnetic radiation, gamma radiation, beta radiation, ethylene oxide, gaseous hydrogen peroxide, liquid hydrogen peroxide, formalin, glutaraldehyde, and/or peracetic acid.

24. A process for determining the effectiveness of sterilization, comprising:
exposing at least one article to be sterilized and the sterilization indicator comprising the biological indicator of claim 1 to a sterilization medium; and
contacting the biological indicator with the at least one inducer and the at least one enzyme substrate to determine the effectiveness of the sterilization.

25. The process of claim 24 wherein the inducer comprises xylose.

26. The process of claim 24 wherein the enzyme substrate comprises: one or more fluorogenic 4-methylumbelliferyl derivatives; one or more diacetylfluorescein derivatives; or a mixture of two or more thereof.

27. The process of claim 24 wherein the enzyme substrate comprises: 4-methylumbelliferyl-beta-D-galactoside.

28. The process of claim 24 wherein the enzyme substrate comprises fluorescein di-(beta-D-galacto-pyranoside).

29. The process of claim 24 wherein: the enzyme substrate comprises one or more 5-bromo-4-chloro-3-indolyl derivatives; one or more nitrophenyl derivatives; one or more indoxyl derivatives; one or more and phenolphthalein derivatives; or a mixture of two or more thereof.

30. The process of claim 24 wherein the enzyme substrate comprises 5-bromo-4-chloro-3-indoxyl-beta-D-galactopyranoside.

31. The process of claim 24 wherein the enzyme substrate comprises: one or more p-nitrophenol derivatives; one or more o-nitrophenol derivatives; or a mixture of two or more thereof.

32. The process of claim 24 wherein the enzyme substrate comprises: nitrophenyl-beta-galactopyranoside; 2-naphthyl-beta-D-galacto-pyranoside; or a mixture thereof.

33. The process of claim 24 wherein the enzyme substrate comprises 5-bromo-4-chloro-3-indolyl-β-D-galactopyranoside.

34. The process of claim 24 wherein the enzyme substrate comprises 4-methylumbelliferone-β-D-galactopyranoside.

35. The process of claim 24 wherein the enzyme substrate comprises 5-Bromo-4-chloro-3-indolyl-β-D-galactopyranoside, 5-Bromo-6-chloro-3-indolyl-β-galactopyranoside), 5-Bromo-3-indolyl-β-D-galactopyranoside, 6-Bromo-2-naphthyl-β-D-galactopyranoside, 6-chloro-3-indolyl-β-D-galacotpyranoside, 3-Indoxyl-β-D-galactopyranoside, 5-Iodo-3-indoxyl-β-D-galactopyranoside, N-methylindoxyl-β-D-galactopyranoside, 2-Nitrophenyl-β-D-galactopyranoside, 4-Nitrophenyl-β-D-galactopyranoside, Phenyl-β-D-galactopranoside, 4-methylumbelliferyl-β-D-galactopyranoside, 4-trifluoromethylumbelliferyl-β-D-galactopyranoside, Fluorescein di(β-D-galactopyranoside), Fluorescein mono-β-D-galactopyranoside, 2-Napthyl-β-D-galactopyranoside, 8-Hydroxyquinoline-β-D-galactopyranoside, Resorufin β-D-galactopyranoside, 3-Carboxyumbelliferyl-β-D-galactopyranoside, 4-Chloromethyl-6,8-difluoroumbelliferyl-β-D-galactopyranoside, 6,8-Difluor-4-methylumbelliferyl-β-D-galactopyranoside, 6,8-Difluoro-4-heptadecylumbelliferyl-β-D-galactopyranoside, 5-(Pentafluorobenzoylamino)-fluorescein-β-D-galactopyranoside, C2-fluorescein-β-D-galactopyranoside, C8-fluorescein-β-D-galactopyranoside, C12-fluorescein-β-D-galactopyranoside, 5-Chloromethylfluorescein-β-D-galactopyranoside, and/or C12-resorufin-β-D-galactopyranoside.

* * * * *